(12) United States Patent
Kennedy et al.

(10) Patent No.: US 7,928,272 B2
(45) Date of Patent: Apr. 19, 2011

(54) CONVERSION OF FLUOROCARBONS

(75) Inventors: Eric Miles Kennedy, The Hill (AU);
Bogdan Zygmunt Dlugogorski, Raymond Terrace (AU)

(73) Assignee: Pacifitech Pty Limited, Sydney (AU)

( * ) Notice: Subject to any disclaimer, the term of this patent is extended or adjusted under 35 U.S.C. 154(b) by 0 days.

(21) Appl. No.: 12/585,401

(22) Filed: Sep. 14, 2009

(65) Prior Publication Data

US 2010/0145110 A1    Jun. 10, 2010

Related U.S. Application Data

(63) Continuation of application No. 12/230,177, filed on Aug. 25, 2008, now abandoned, which is a continuation of application No. 10/548,589, filed as application No. PCT/AU2004/000297 on Mar. 12, 2004, now abandoned.

(30) Foreign Application Priority Data

Mar. 12, 2003 (AU) ................ 2003100187

(51) Int. Cl.
*C07C 21/18* (2006.01)
(52) U.S. Cl. .................... 570/159; 570/172
(58) Field of Classification Search .......... None
See application file for complete search history.

(56) References Cited

U.S. PATENT DOCUMENTS

| | | | |
|---|---|---|---|
| 2,687,440 A | 8/1954 | McGrew et al. | |
| 3,428,695 A | 2/1969 | Soulen et al. | |
| 5,382,719 A | 1/1995 | Fagan | |
| 5,386,068 A | 1/1995 | Lantz et al. | |
| 6,096,932 A | 8/2000 | Subramanian | |

FOREIGN PATENT DOCUMENTS

| | | |
|---|---|---|
| GB | 979618 | 1/1965 |
| WO | WO 99/07443 | 2/1999 |
| WO | WO 01/06830 A2 | 2/2001 |

OTHER PUBLICATIONS

Li et al Chem.Eng.Sci., 2000, 55, 4067-4078.*
Li, K., et al; "Experimental and computational studies of the pyrolysis of $CBrF_3$, and the reaction of $CBrF_3$ with $CH_4$"; *Chemical Engineering Science*, 55; pp. 4067-4078 (2000).
Examination Report dated Jan. 11, 2010, in counterpart Australian Patent Application No. 2004220475, 3 pages.
Tran et al., "Gas-Phase Reaction of Halon 1211 ($CBrClF_2$) with Methane," Ind. Eng. Chem. Res., 2001, 40:3139-3143.

* cited by examiner

*Primary Examiner* — Sudhakar Katakam
(74) *Attorney, Agent, or Firm* — The Marbury Law Group PLLC

(57) ABSTRACT

A process is disclosed for the conversion of fluorocarbons into fluorinated unsaturated compounds useful as monomers or other chemical precursors, such as $C_2H_2F_2$. The process comprises reacting a hydrocarbon feed (20) and a fluorocarbon feed (10) in a high temperature reactor (26), at sufficiently high temperature and sufficiently short resident time to form a reaction product mixture (28) having the fluorinated unsaturated compound as the major reaction product, and cooling (18) to a temperature sufficiently low to inhibit polymerization of the unsaturated compound. The reaction product may then be processed by removal of higher molecular weight compounds (35) and acids (32) and optionally separated (44) into product components.

4 Claims, 4 Drawing Sheets

CONVERSION OF FLUOROCARBONS

This application is a continuation of application Ser. No. 12/230,177, filed Aug. 25, 2008 now abandoned, which is a continuation of application Ser. No. 10/548,589, filed Sep. 12, 2005 now abandoned, which is a 371 of PCT/AU2004/000297, filed Mar. 12, 2004, the entire content of which is hereby incorporated by reference in this application.

FIELD OF THE INVENTION

The present invention relates to a process for the conversion of fluorocarbons, being organic compounds having C—F bonds—and including hydrofluorocarbons, halofluorocarbons, hydrohalofluorcarbons—and in particular to their conversion into fluorinated unsaturated compounds having economic use, such as monomers.

BACKGROUND OF THE INVENTION

Fluorocarbons have been found to have many uses, for example the use of fluorocarbons, halofluorocarbons and hydrofluorocarbons as refrigerants and propellants, halons (ie. chlorinated and/or brominated saturated fluorocarbons) as flame suppressants used in fire fighting and perfluorocarbon as foam blowing agents However, many of these useful fluorinated compounds have been found to be damaging to the environment, and/or to humans. The use and production of some fluorocarbons are now restricted or banned under international treaties.

Enormous stockpiles of halons, chlorofluorocarbons (CFCs) and other fluorocarbon pollutants exist internationally, and there is a need for techniques for their disposal.

Techniques for disposal of these fluorocarbon pollutants include destructive processes such as incineration and argon plasma destruction. Such processes are expensive to run, result in incomplete destruction of the fluorocarbons and produce compounds of no particular economic value. Plasma destruction is suitable for dilute concentrations of some fluorocarbons, but not for halons in view of their flame suppressive properties. Other proposed disposal processes include hydrolysis, steam reforming, dehalogenation and dehydrohalogenation. However, incineration remains the most widely adopted technology for fluorocarbon disposal.

Other processes have been proposed for conversion of fluorocarbon pollutants into compounds of economic value.

WO 99/07443 disclosed a method of conversion of halons 1301 ($CF_3Br$) and 1211 ($CFCl_2Br$) by reaction with methane to produce $CF_3H$, $CH_3Br$ and a range of minor products.

Li, K., Kennedy, E. M., and Dlugogorski B. Z., Experimental and Computational Studies of the Pyrolysis of $CBrF_3$, and the Reaction of $CBrF_3$ with $CH_4$, *Chemical Engineering Science*, 55 (2000) 4067-4078, compared theoretical and experimental reaction product profiles from the hydrodehalogenation reaction of halon 1301 with methane. The primary reaction product found was $CHF_3$, with $CH_3Br$ and $C_2H_2F_2$ produced in lesser quantities. The authors used the experimental results to refine the theoretical reaction modelling for the hydrodehalogenation reaction.

SUMMARY OF THE INVENTION

The present inventors have now discovered that, under certain process conditions, fluorocarbons can be reacted with a hydrocarbon to produce as a major reaction product fluorinated unsaturated $C_2$ or higher compounds useful as chemical precursors, and especially as monomers.

The present invention thus aims to provide a process for converting fluorocarbon pollutants—such as halons, fluorocarbons, hydrofluorocarbons, halofluorocarbons or perfluorocarbons—into a source of fluorinated unsaturated compounds useful in their own right or as precursors for production of other molecules, including polymers.

In one form, the present invention provides a process for production of fluorinated $C_2$ or higher unsaturated compounds from reaction of a hydrocarbon with a fluorocarbon feed, including the steps of:

(a) reacting a hydrocarbon or hydrocarbon mixture with a fluorocarbon feed under non-oxidative conditions in a high temperature reactor, at sufficiently high temperature and sufficiently short residence time to form a reaction product mixture having a fluorinated unsaturated compound as the major reaction component thereof, (b) rapidly cooling said reaction product mixture to a temperature sufficiently low to substantially inhibit polymerisation of said fluorinated unsaturated compound.

In one preferred form, the invention further includes the steps of (c) condensing higher boiling point compounds from said cooled reaction product mixture, (d) removing hydrogen halide acids from the reaction product mixture, optionally (e) separating said fluorinated unsaturated $C_2$ or higher compound from said reaction product mixture, and optionally (f) recycling at least a portion of the remainder of said reaction product mixture from step (e) to said reactor.

As used herein, the term "fluorocarbon" refers to organic compounds having C—F bonds, including hydrofluorocarbons, halofluorocarbons, hydrohalofluorcarbons.

Suitable fluorocarbons for conversion according to the invention include $CCl_2F_2$, $CFCl_2Br$, $CF_3Br$, $CF_3H$, $CHClF_2$, $C_4F_{10}$, $CH_2F_2$, $CF_3H$, $C_3F_8$ and $C_3F_8O$. Preferably, the fluorocarbon feed includes a halofluorocarbon selected from $CF_3Br$, $CF_2ClBr$ or $CCl_2F_2$. Preferred fluorinated unsaturated $C_2$ or higher reaction compounds are those adapted for use as monomers, such as $CF_2CFH$, $C_2H_3F$ and $C_2H_2F_2$, most preferably $C_2H_2F_2$.

It is strongly preferred that the fluorocarbon is at least 30% concentrated, more preferably at least 50% concentrated and most preferably 90% or higher concentrated.

Preferably, the reaction is conducted at a temperature of about 950-1300K, more preferably about 1050-1200K, and most preferably from 1050-1150K.

BRIEF DESCRIPTION OF THE DRAWINGS

Further preferred forms of the invention will now be described with reference to the Examples and to the accompanying drawings, in which.

DETAILED DESCRIPTION OF THE PREFERRED EMBODIMENTS

Figure 1:
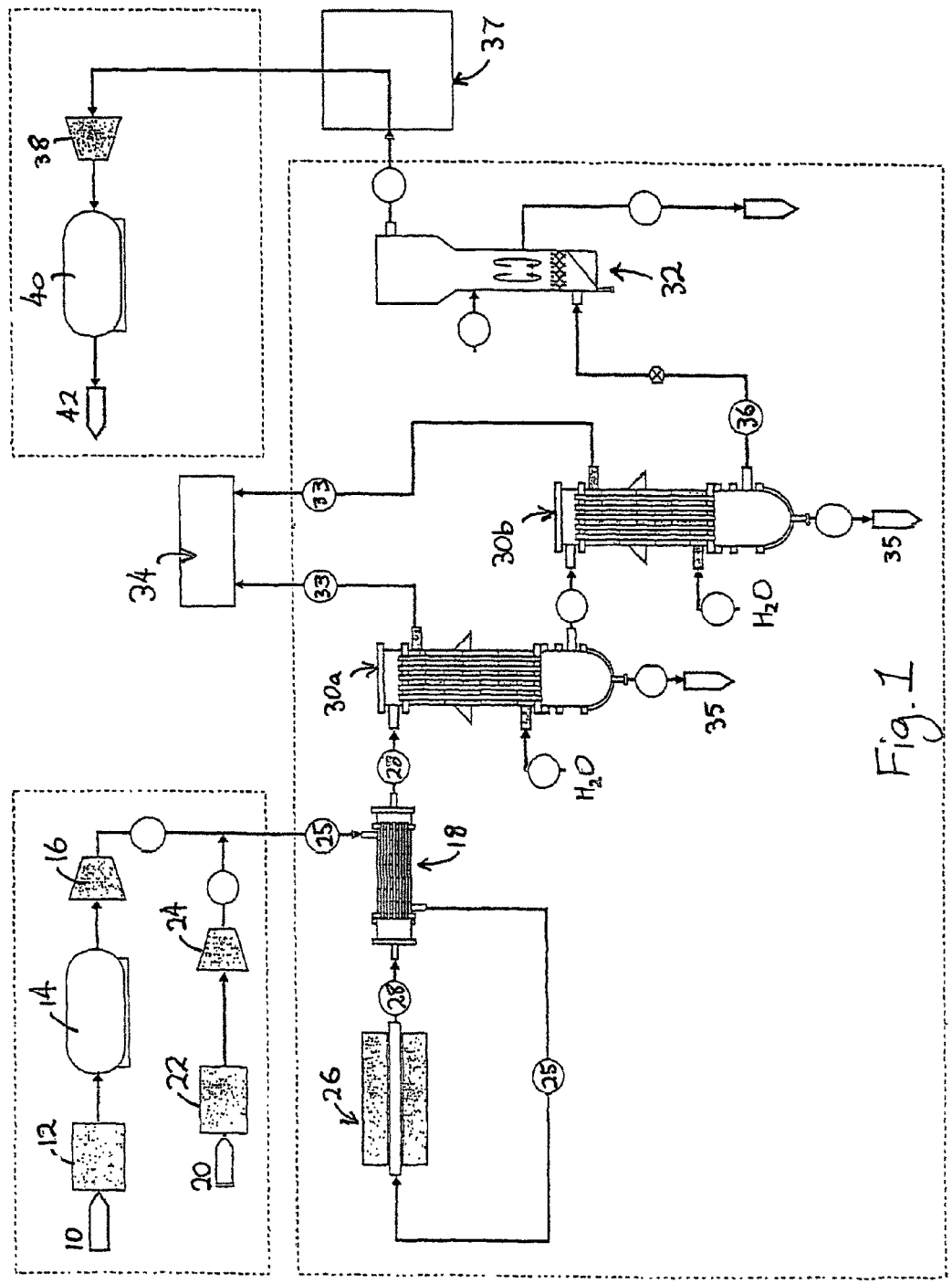
FIG. 1 is a process flow diagram according to first preferred embodiment of the invention.

With reference to FIG. 1, a fluorocarbon feed 10—which, as previously described, may include halofluorocarbons or hydrofluorocarbons—is fed via a decanting manifold 12, feed buffer tank 14 and fluorocarbon feed compressor 16 to a reaction feed pre-heater 18.

The hydrocarbon feed 20—which may be a single hydrocarbon such methane, ethane or propane, or a mixed hydrocarbon source such as natural gas—is optionally pre-processed by removal of $CO_2$ and $H_2O$ at 22 and fed via a hydrocarbon feed compressor 24 to the feed pre-heater 18.

The fluorocarbon 10 and hydrocarbon 20 feeds may be brought together prior to or at the feed pre-heater 18, as shown in FIG. 1, providing the temperature of the preheated mixture is kept below about 850-900K to prevent premature initiation of the reaction. Preferably, the hydrocarbon is fed to the reactor in excess, for example at a molar ratio of hydrocarbon to fluorocarbon of less than about 2:1, more preferably less than about 1.5:1.

Reactor 26 may be a gas phase or a catalytic reactor, heated by electric heating elements or similar to sustain a reaction temperature sufficient to initiate reaction of the fluorocarbon and hydrocarbon feed mixture but insufficient to cause instant polymerisation of the fluorinated unsaturated reaction product. The optimum reaction temperature will depend on the particular fluorocarbon and hydrocarbon being reacted, and the reactor residence time.

For halons, a suitable reaction temperature will be about 1050-1100K, whereas for chlorofluorocarbons slightly higher temperatures, such as about 1100-1150K, will be suitable to optimise the balance between conversion of the fluorocarbon to unsaturated fluorinated product against uncontrolled polymerisation of the product.

A generic reaction mechanism is:

$C_aH_b$ hydrocarbon $\rightarrow C_aH_{b-x}+xH$ $C_cF_mY_n \rightarrow C_cF_{(m-1,2,\text{or }3)}+nY+(m-1,2,\text{or }3)F$ $C_aH_{b-x}+C_cF_{(m-1,2,\text{or }3)} \rightarrow C_{a+b-x}F_{(m-1,2,\text{or }3)}+nHY+(m-1,2,\text{or }3)HF$ Where $C_cF_mY_n$ is any fluorocarbon containing one or more C—F bonds and Y represents any heteroatom, especially halogen(s) such as chlorine, bromine or iodine. $C_{a+c}H_{b-x}F_{(m-1,2,\text{or }3)}$ is an unsaturated hydrofluorocarbon.

Each reaction step may be gas phase or catalytic, or a combination thereof.

Suitable gas phase reactors 26 include plug flow reactors, such as an alumina tubular plug flow reactor having a relatively low volume compared to the flow rate of reaction gases, so that residence time of the fluorocarbon feed at reaction temperature is short. For example, at a bench scale, a reactor volume of about 1 cm with a fluorocarbon feed flow of 10 $cm^3/s$ will give a residence time of about 100 ms.

Preferred residence times range from about 0.01 s to 0.5 s, more preferably about 0.02-0.15 s, and most preferably under about 0.1 s, based on the fluorocarbon feed rate. As mentioned above, the optimal residence time will depend on the temperature and the particular reaction, so that the use of temperatures at the lower end of the preferred range will require higher residence time. The use of higher temperatures and shorter residence times is preferred, as this will assist in maximising the yield of $C_2H_2F_2$ or other unsaturated fluorinated compound as the major component of the reaction product mixture.

Suitable catalyst systems for catalytic reactors include rare earth oxides (eg. $Sm_2O_3$, $La_2O_3$, $Pr_6O_{11}$), alkali earth metal oxides (eg. BaO, CaO, MgO), zeolite catalysts (eg. HZSM5), metal ion exchanged zeolites (eg, REY) and known methane activation catalysts (eg. Li/MgO, PbO). It is also expected that super acid catalysts (eg. $ZrO_2$) and $AlF_3$ and other fluorinated metals will be suitable. Again, the reactor volume is small, to give a short residence time.

The reaction product mixture 28 from the reactor 26 passes immediately to the feed pre-heater 18, which is a heat exchanger which cools the product mixture to a point at which further reaction of the product mixture, and in particular polymerisation of the $C_2H_2F_2$, $CH_3F$ or other fluorinated unsaturated components of the reaction product mixture 28, is inhibited.

The cooled reaction product mixture from the heat exchanger 18 passes to a series of water-cooled condensers 30a, 30b, to condense and separate high boiling point, oily components 35 from the mixture.

The gaseous output 36 from the last condenser 30b passes to a fluidised bed caustic scrubber 32, in which the mineral acids HCl, HBr and HF are stripped from the mixture. The fluidised and reacting media is CaO (lime), with the scrubber operating at approximately 150° C.

The water 33 from the condensers is passed to a water cooling circuit 34.

Where the product is to be sold as a mixture, for subsequent refining and use by the customer, the gaseous output from the scrubber 32 may be passed through a filtration stage such as bag filter unit 37 then to a product compressor 38, product buffer tank 40 and discharge 42.

Figure 2:
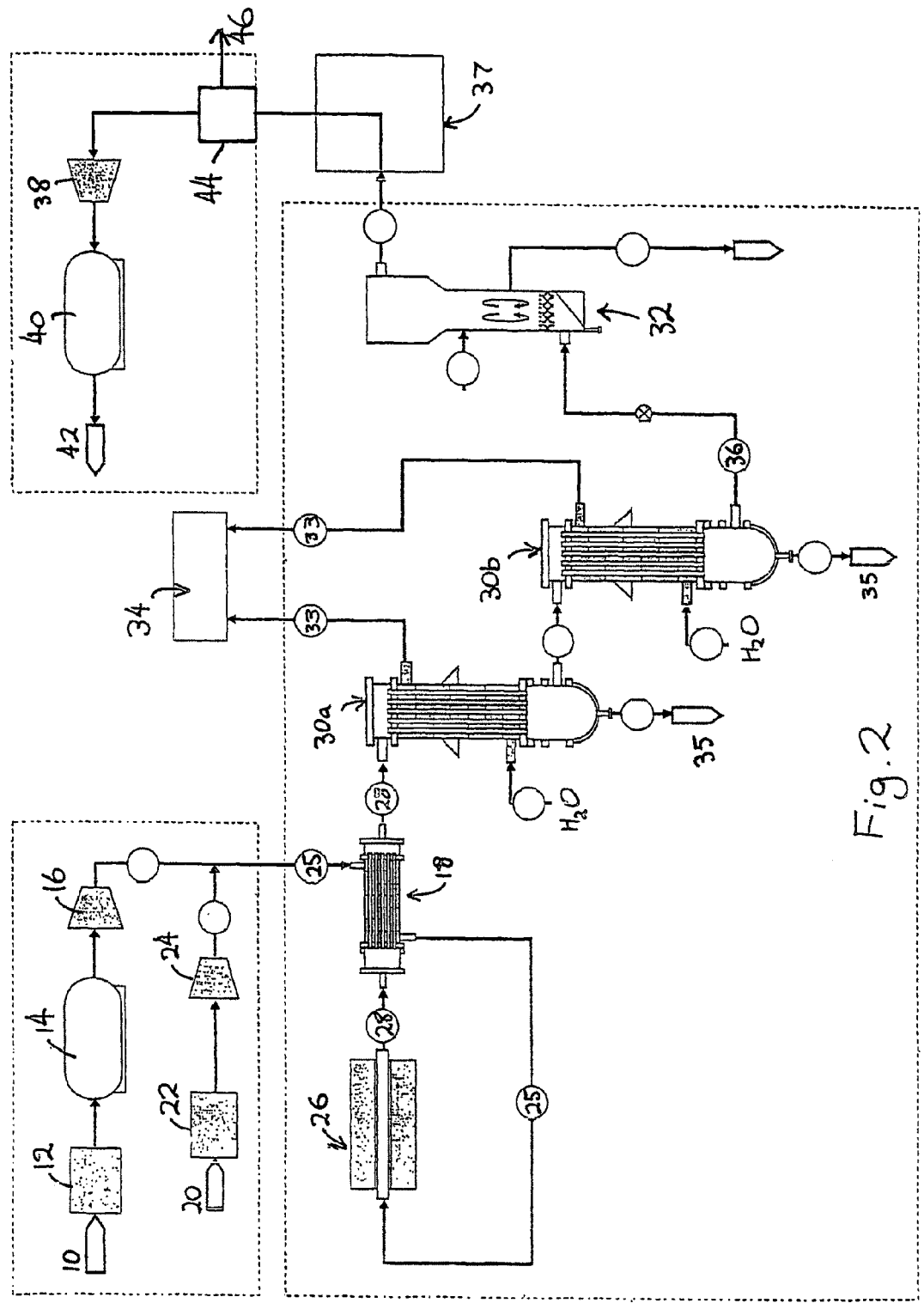
FIG. 2 is a process flow diagram of a second embodiment.

The process of FIG. 2 is similar to FIG. 1, but with an additional separation step 44 for separation of the $C_2H_2F_2$ following the bag unit 37. Depending on the economics of the process, the unreacted hydrocarbon and/or other reaction products may optionally be recycled back to the reactor 26. Suitable separation means may include distillation, membrane or solvent separation, a combination thereof, or other suitable methods.

The fluorinated unsaturated compounds produced by the process are a valuable resource, useful as chemical precursors such as monomers for the production of fluorelastomers. For example, difluorethylene ($C_2H_2F_2$) is a monomer which when polymerised forms a temperature and corrosion resistant fluoropolymer.

Example 1

Halon 1211 ($CF_2ClBr$) of purity >99% and natural gas were mixed and passed through a 1 $cm^3$ gas phase, alumina plug flow reactor at a molar ratio of approximately 1:1 (feed rates of 14.0 for halon 1211 and 15.0 mmol/h methane) and temperatures of ranging between 773K and 1173K at 50K increments. The residence time was 60 ms. The reaction products were cooled and analysed.

The analysis of the major components of the natural gas used in this experiment was:

| | |
|---|---|
| $CH_4$ | 95.1% (88.89) |
| $C_2H_6$ | 0.1% (7.59) |
| $C_3H_8$ | 0.1% (0.14) |
| $C_4H_{10}$ | 0.01% (0.21) |
| $CO_2$ | 2.5% (1.88) |
| $N_2$ | 1.4% (1.23) |
| Argon | 0.5% (0.06) |

Shown in brackets is a typical natural gas composition as quoted by the gas supplier, The Australian Gas Light Company of North Sydney, Australia. It is not believed that the differences between the gas composition used and the quoted typical composition, and in particular the proportions of methane and ethane, had a substantial effect on the experimental results.

The experiment was repeated with a molar ratio of approximately 1:2 (feed rates of 14.1 mmol/hr for the halon 1211 and 28.0 mmol/h methane), a residence time of approximately 60 ms, and temperatures from 873K to 1173K.

Figure 3:
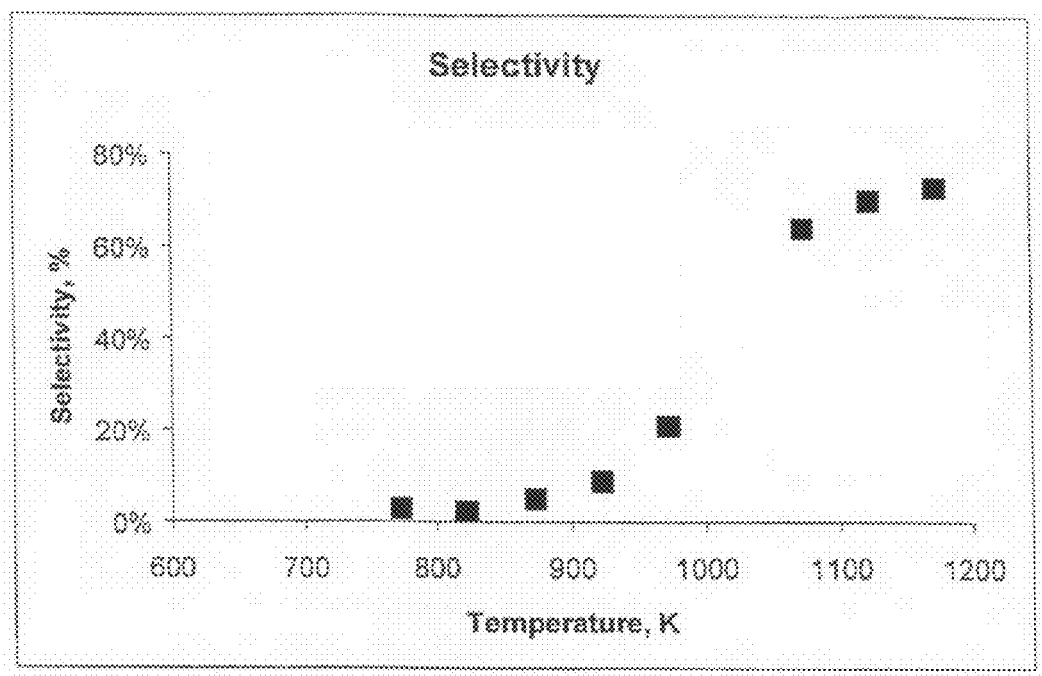
FIG. 3 is a graph of Selectivity against Temperature for Example 1.

Table 1 shows the consumption rates of the feed species and formation rates for both major and minor reaction products, in mmol/hr, and the "missing carbon"—ie. the percentage of the feed carbon which is lost as non-gaseous reaction products. Table 2 shows the variation against temperature of the halon conversion, selectivity of $C_2H_2F_2$ (as a proportion of gaseous reaction products, excluding unreacted halon and natural gas) and $C_2H_2F_2$ yield figures for the 1:1 feed reaction, and FIGS. 3-5 show these graphically.

Figure 4:
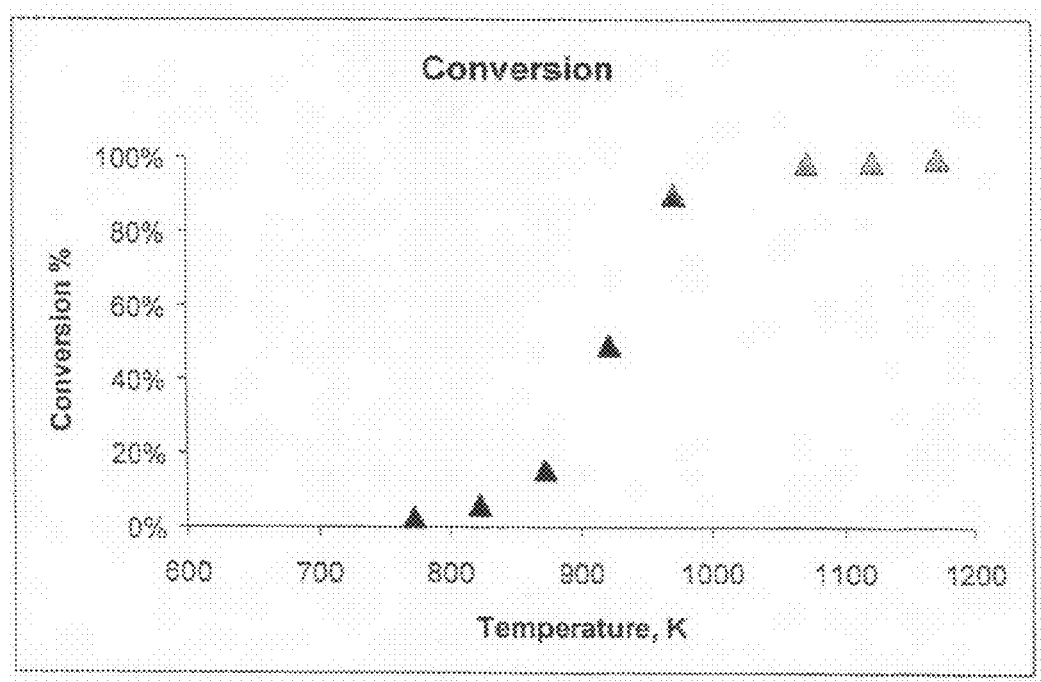
FIG. 4 is a graph of Conversion against Temperature for Example 1.

Referring to Tables 1 and 2 and FIG. 4, it can be seen that at temperatures of greater than about 1000-1050K the reaction approaches essentially 100% conversion of the halon. With reference also to FIG. 3, above about 1050K, $C_2H_2F_2$ becomes the major reaction product of the reaction with selectivity (as a percentage of gaseous reaction products, excluding unreacted halon and natural gas) exceeding 60%. However, as the reaction temperature increases further, above about 1150K, the percentage of "missing carbon" in the form of solid deposits—believed to be polymerisation products of the $C_2H_2F_2$ and $C_2H_3F$—increases.

Figure 5:
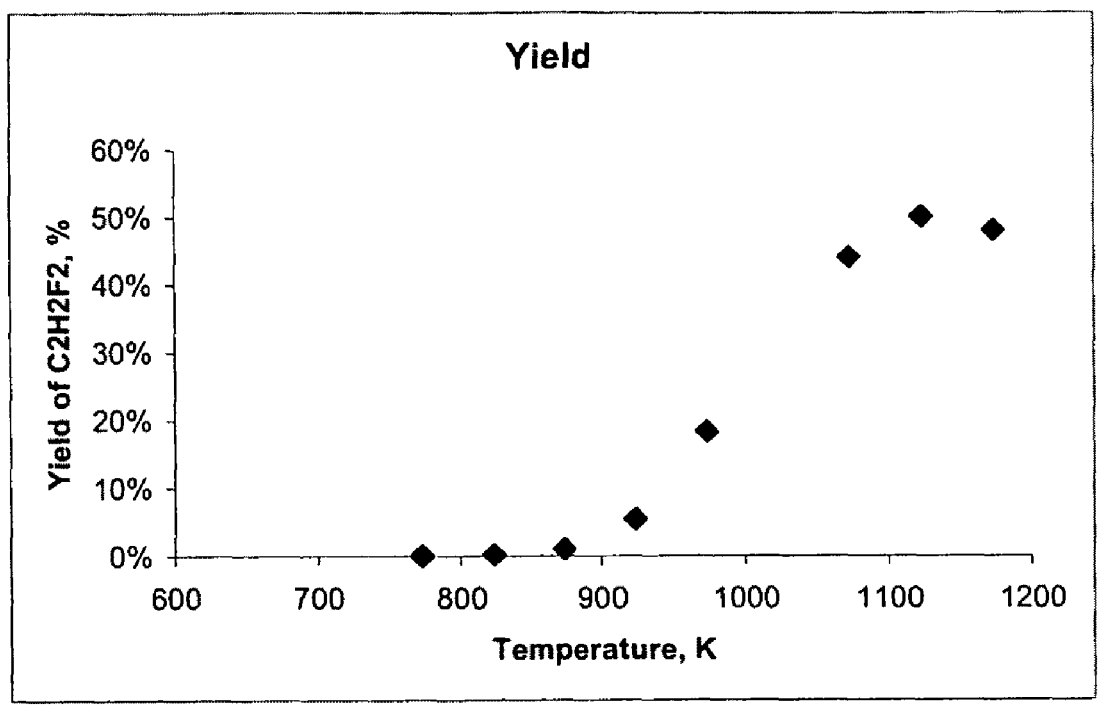
FIG. 5 is a graph of Yield against Temperature for Example 1.

With reference to FIG. 5, it can be seen that the yield of $C_2H_2F_2$—calculated as the selectivity multiplied by the conversion—peaks at about 50% at approximately 1100K and then begins to decline with increasing temperature as more of the product is lost to polymerisation.

It can also be seen by comparison of the 1:1 and 1:2 reaction results in Table 1 that feeding the hydrocarbon in slight excess increases the selectivity toward $C_2H_2F_2$ and reduces the carbon lost as carbon deposits. It is preferred however that the molar ratio of fluorocarbon to hydrocarbon be kept less than about 1:1.5, and more preferably about 1:1.3 due to the cost of raising the excess hydrocarbon to the reaction temperature.

TABLE 2

Conversion, Selectivity and Yield against Temperature

| Temperature (K) | Conversion | Selectivity | Yield |
|---|---|---|---|
| 773 | 0.025 | 0.028571 | 0.000714 |
| 823 | 0.058571 | 0.021505 | 0.001429 |
| 873 | 0.152857 | 0.049342 | 0.010714 |
| 923 | 0.490714 | 0.088372 | 0.054286 |
| 973 | 0.896429 | 0.208266 | 0.183571 |
| 1073 | 0.982857 | 0.640706 | 0.440714 |
| 1123 | 0.986429 | 0.699601 | 0.500714 |
| 1173 | 0.994286 | 0.728355 | 0.480714 |

TABLE 1

Thermal hydrodehalogenation of halon 1211 ($CBrClF_2$) with natural gas

| Reactant (mmol/h) $CBrClF_2:CH_4$ ratio | Temperature (K) | Consumption (mmol/h) | | Rate of Formation (mmol/h) Major Products | | | Minor Products | | | |
|---|---|---|---|---|---|---|---|---|---|---|
| | | $CBrClF_2$ | $CH_4$ | $CHClF_2$ | $CH_3Br$ | $C_2H_2F_2$ | $CHF_3$ | $CH_3Cl$ | $CCl_2F_2$ | $CBr_2F_2$ |
| 14.0:15.0 | 773 | 0.35 | 0.2 | 0.06 | 0.16 | 0.01 | 0.04 | trace | 0.05 | 0.02 |
| | 823 | 0.82 | 0.6 | 0.28 | 0.49 | 0.02 | 0.01 | 0.01 | 0.07 | 0.02 |
| | 873 | 2.14 | 1.66 | 1.25 | 1.36 | 0.15 | 0 | 0.03 | 0.08 | 0.01 |
| | 923 | 6.87 | 4.72 | 3.78 | 2.8 | 0.76 | 0.01 | 0.08 | 0.1 | 0.02 |
| | 973 | 12.55 | 8.75 | 3.1 | 3.22 | 2.57 | 0.01 | 0.11 | 0.12 | 0.03 |
| | 1073 | 13.76 | 11.44 | 0.29 | 0.71 | 6.17 | 0.07 | 0.1 | 0.12 | trace |
| | 1123 | 13.81 | 12 | 0.15 | 0.21 | 7.01 | 0.08 | 0.09 | 0.11 | nd |
| | 1173 | 13.92 | 12.74 | 0.12 | 0.06 | 6.73 | 0.05 | 0.07 | 0.06 | nd |
| 14.1:28.0 | 873 | 2.09 | 1.7 | 1.53 | 1.66 | 0.19 | 0.04 | trace | 0.05 | 0.02 |
| | 923 | 7 | 5 | 4.01 | 3.69 | 0.97 | trace | 0.01 | 0.07 | 0.02 |
| | 973 | 12.5 | 9.2 | 3.28 | 4.74 | 3.25 | nd | 0.03 | 0.08 | 0.01 |
| | 1023 | 13.84 | 11.3 | 0.71 | 3.51 | 6.1 | 0.01 | 0.08 | 0.11 | 0.02 |
| | 1073 | 13.88 | 12.2 | 0.18 | 1.59 | 7.95 | trace | 0.11 | 0.12 | 0.03 |
| | 1123 | 13.93 | 12.7 | 0.06 | 0.42 | 8.6 | 0.07 | 0.11 | 0.13 | nd |
| | 1173 | 14.03 | 14.23 | 0.05 | 0.08 | 8.83 | 0.51 | 0.18 | 0.05 | nd |

| Reactant (mmol/h) $CBrClF_2:CH_4$ ratio | Temperature (K) | Rate of Formation (mmol/h) Minor Products | | | | | | "Missing Carbon" as % of Feed |
|---|---|---|---|---|---|---|---|---|
| | | $C_2F_4$ | $C_2H_3F$ | $C_3H_3F_5$ | $C_3H_2F_6$ | $C_2H_2Cl$ | $C_2HClF_2$ | |
| 14.0:15.0 | 773 | tarce | nd | nd | nd | nd | 0.01 | 0.7 |
| | 823 | 0.02 | nd | nd | nd | nd | 0.01 | 1.5 |
| | 873 | 0.1 | nd | nd | nd | nd | 0.06 | 1.6 |
| | 923 | 0.47 | 0.01 | trace | 0.09 | 0.05 | 0.43 | 3.8 |
| | 973 | 1.4 | 0.05 | 0.02 | 0.43 | 0.22 | 1.06 | 9.5 |
| | 1073 | 0.25 | 0.38 | 0.26 | 0.92 | 0.15 | 0.21 | 20.9 |
| | 1123 | 0.56 | 0.56 | 0.28 | 0.81 | 0.1 | 0.06 | 18.3 |
| | 1173 | 0.64 | 0.66 | 0.2 | 0.6 | 0.03 | 0.02 | 26.7 |
| 14.1:28.0 | 873 | trace | nd | nd | nd | nd | 0.01 | 0.3 |
| | 923 | 0.02 | nd | nd | nd | nd | 0.02 | 5.2 |
| | 973 | 0.1 | nd | nd | nd | nd | 0.06 | 16 |
| | 1023 | 0.47 | 0.01 | trace | trace | trace | 0.42 | 15.2 |
| | 1073 | 1.4 | 0.05 | 0.02 | 0.43 | 0.22 | 1.06 | 3.2 |
| | 1123 | 0.25 | 0.38 | 0.25 | 0.92 | 0.15 | 0.21 | 7.5 |
| | 1173 | trace | 1.14 | 0.19 | 0.67 | 0.01 | trace | 11.5 |

*nd: not detected

While Example 1 is described with reference to the thermal hydrodehalogenation of halon 1211 to form difluoroethene, it is believed that the reaction may occur by creation of $CF_2$:di-radicals from the fluorocarbon and reaction of those di-radicals with the hydrocarbon moiety, and thus is applicable to conversion of a much broader range of fluorocarbons, with adjustment of optimal reaction temperature and residence times. In particular, it is known that the process is suitable, under generally similar reaction conditions, to conversion of other fluorocarbons, eg. halon 1301, and CFC-12 (dichlorodifluoromethane), $CF_3H$, $CHClF_2$, $C_4F_{10}$, $CH_2F_2$, $CF_3H$, $C_3F_8$ and $C_3F_8O$. Furthermore, the process may be used to produce other unsaturated fluorinated compounds of economic value, such as $C_2H_3F$.

In this specification, the word "comprising" is to be understood in its "open" sense, that is, in the sense of "including", and thus not limited to its "closed" sense, that is the sense of "consisting only of". A corresponding meaning is to be attributed to the corresponding words "comprise, comprised and comprises where they appear.

While particular embodiments of this invention have been described, it will be evident to those skilled in the art that the present invention may be embodied in other specific forms without departing from the essential characteristics thereof. The present embodiments and examples are therefore to be considered in all respects as illustrative and not restrictive, the scope of the invention being indicated by the appended claims rather than the foregoing description, and all changes which come within the meaning and range of equivalency of the claims are therefore intended to be embraced therein. It will further be understood that any reference herein to known prior art does not, unless the contrary indication appears, constitute an admission that such prior art is commonly known by those skilled in the art to which the invention relates.

The invention claimed is:

1. A process for production of $C_2H_2F_2$ from reaction of at least one of a methane or natural gas with a fluorocarbon feed, comprising the steps of:
   (a) reacting the at least one of methane or natural gas with the fluorocarbon feed under non-oxidative conditions in a high temperature reactor, at a temperature of above about 1150K and a residence time under 0.1 seconds to form a reaction product mixture having the $C_2H_2F_2$ as the major reaction component thereof;
   (b) cooling said reaction product mixture to a temperature sufficiently low to substantially inhibit polymerization of the $C_2H_2F_2$;
   wherein:
   said fluorocarbon feed is selected from the group consisting of hydrofluorocarbons, halofluorocarbons and hydrohalofluorocarbons;
   a selectivity of $C_2H_2F_2$ as a percentage of gaseous reaction products excluding unreacted fluorocarbon and at least one of methane and natural gas exceeds 60%; and
   a yield of $C_2H_2F_2$ exceeds about 44%.

2. A process according to claim 1, wherein said fluorocarbon feed is selected from the group consisting of $CCl_2F_2$, $DF_2ClBr$, $CF_3Br$, $CF_3H$, $CHClF_2$, $C_4F_{10}$, $CH_2F_2$, $CF_3H$, $C_3F_8$ and $C_3F_8O$.

3. A process according to claim 2, wherein said fluorocarbon feed is $CF_2ClBr$.

4. A process according to claim 1, wherein said reaction residence time is from 0.01 second to under 0.1 seconds and said reaction is conducted at a temperature of above 1150K to 1300K.

* * * * *